United States Patent [19]

Pastorek et al.

[11] Patent Number: 5,066,806
[45] Date of Patent: Nov. 19, 1991

[54] NOVEL SEPARATION PROCESS

[75] Inventors: Emmerich Pastorek, Hemsbach; Winfried Orth, Hassloch; Wolfgang Weiss, Neckarhausen; Hans W. Kleffner, Battenberg, all of Fed. Rep. of Germany

[73] Assignee: Rutgerswerke AG, Fed. Rep. of Germany

[21] Appl. No.: 566,961

[22] Filed: Aug. 13, 1990

[30] Foreign Application Priority Data

Sep. 27, 1989 [DE] Fed. Rep. of Germany ....... 3932136

[51] Int. Cl.$^5$ ........................................... C07D 215/18
[52] U.S. Cl. ................................................... 546/180
[58] Field of Search ................ 546/152, 180; 564/425, 564/438

[56] References Cited

U.S. PATENT DOCUMENTS 4,996,324  2/1991  Bott et al. ........................... 546/152

Primary Examiner—Mary C. Lee
Assistant Examiner—Robert Whittenbaugh
Attorney, Agent, or Firm—Bierman and Muserlian

[57] ABSTRACT

A process for the recovery of isomeric pure 7-chloro-quinaldine from isomeric mixtures of chloro-quinaldines comprising dissolving the isomeric mixture of chloro-quinaldines in an organic solvent, adding an aqueous tartaric acid solution to the organic solution to form the tartrate of 7-chloro-quinaldine in crystalline form, recovering the crystals and treating the same with a base to obtain 7-chloro-quinaldine.

9 Claims, No Drawings

NOVEL SEPARATION PROCESS

STATE OF THE ART 7-chloro-quinaldine serves as an intermediate product for the production of pharmaceuticals as described for instance in EP 219,308 A2.

Methods for the production of 7-chloro-quinaldine are known from the literature and they involve modified processes of the quinoline synthesis according to Skraup of the year 1880 and of the reaction found by Doebner and Miller in 1881. Quinaldines substituted in the 7-position are by these methods synthesized from meta-aniline, and hence the desired 7-chloro-quinaldine from m-chloroaniline. Using 3-chloro-nitrobenzene or the sodium of 3-nitro-benzene-sulfonic acid as oxidant, the aniline derivative is reacted in sulfuric acid or hydrochloric acid with an aldehyde such as crotonaldehyde.

The cyclization leads to an isomer mixture of predominantly 5- and 7-chloro-quinaldines with the total yield and the isomer ratio being influenced by the concentration of the sulfuric acid used. The proportion of the 7-isomer increases with decreasing sulfuric acid concentration, but at the same time the total yield of 5- and 7-isomers decreases.

According to Spivey et al (J. Chem. Soc. 2656-2662 (1949)), an optimum total yield, which corresponds to about 60% of theory, is obtainable with a 60% sulfuric acid with the isomer ratio of 3:1 here shifted in favor of the 7-isomer.

The product mixture can be separated by various methods described in the literature which include crystallization from petroleum ether [Ono, M. et al, Chem. Pharm. Bull., Vol. 34 (2), p. 463 to 470 (1986)], transformation into picrates and subsequent crystallization [Spivey et al., J. Chem. Soc., p. 2656 to 2662 (1949)] or the separation of the 7-chloro-quinaldine as hydrochloride-zinc chloride complexes [Leir, J. Org. Chem., Vol. 42 (5), p. 911 to 913 (1977)].

The crystallization described by Ono et al has the disadvantage that at most only ⅔ of the 7-isomer can be isolated while the rest forms a eutectic mixture with the 5-isomer. Due to the properties of picric acid, the separation by means of picric acid is not suitable for the industrial scale. As experiments have shown, satisfactory separation of the 7-chloro-quinaldine from the 5-isomer is not obtained by the formation of the hydrochloride-zinc chloride complex, so that after release, the zinc impurities and 5-chloro isomer remaining in the product are not compatible with further use for the production of pharmaceuticals.

Another argument against large-scale industrial isomer separation with zinc chloride is ecological compatibility since according to rules of the Environmental Protection Authorities, zinc salts belong to the hazardous substances of Group 2. Accordingly, in the Federal Republic of Germany, for instance, the zinc concentration in waste water must not exceed 0.5 mg/l. Waste water resulting from isomer separation with zinc chloride must therefore be processed at great cost.

Known from the literature are experiments on the separation of the isomer mixture by fractional crystallization of the free bases from alcohol, of the hydrochlorides from acetic acid, and of the oxalates or perchlorates from alcohol. On the whole, these experiments were unsatisfactory because the separation is incomplete and furthermore, undesired salts remain in the product after release of the base. Another, theoretically possible, method is the separation of the isomers by rectification, but it is not promising because of the very small difference in the boiling points.

OBJECTS OF THE INVENTION

It is an object of the invention to provide a simple, practical process for the separation of 7-chloro-quinaldine from isomeric mixtures, particularly from an isomeric mixture of 5-and 7-chloro-quinaldine to obtain a high-purity product suitable for the preparation of pharmaceutical active ingredients in a high yield.

This and other objects and advantages of the invention will become obvious from the following detailed description.

THE INVENTION

The novel process of the invention for the recovery of isomeric pure 7-chloro-quinaldine from isomeric mixtures of chloro-quinaldines comprises dissolving the isomeric mixture of chloro-quinaldines in an organic solvent, adding an aqueous tartaric acid solution to the organic solution to form the tartrate of 7-chloro-quinaldine in crystalline form, recovering the crystals and treating the same with a base to obtain 7-chloro-quinaldine.

To be able to separate a high-purity 7-chloro-quinaldine from a crude product at the lowest possible cost and in high yield, a method of separation is needed by which the 5-chloro-quinaldine can be removed simultaneously with other undesired by-products as well as with unreacted initial compounds, but by which no new impurities get into the product that would preclude its use for the production of pharmaceuticals.

Surprisingly it was found that with the aid of tartaric acid a very good separation of the 7-chloro-quinaldine from the reaction mixture, particularly from the 5-chloro-isomer and from by-products and residues contained in the crude product from the synthesis reaction, can be obtained. While the salt formation with other natural carboxylic acids such as acetic acid or oxalic acid permitted only an unsatisfactory separation, it is possible with tartaric acid to separate 75 to 90% of the 7-chloro-quinaldine contained in the isomer mixture which can be released as the free base in a purity of up to 99%. Therefore, with the process, it is possible to separate from the isomer mixture up to 90% of the 7-chloro-quinaldine formed in the Skraup synthesis.

To carry out the process, the crude product obtained from the Skraup synthesis is taken up in an organic solvent, preferably acetone. Other suitable organic solvents are alcohols, ketones and ethers miscible with water such as acetone, ethanol or ethyl acetate, but also solvents not miscible with water such as toluene or chloroform.

The insoluble residues are separated from the 0.5 to 1.5 molar chloro-quinaldine solution produced and the solution obtained is added with stirring dropwise to an aqueous tartaric acid so that after the addition of the dissolved isomer mixture, a ratio of chloro-quinaldine to tartaric acid of 1:5, preferably 1:1.2, is present in the reaction solution. This addition can take place either at room temperature or at reflux and generally, the dropwise addition is done at about 50° to 80° C., preferably at a temperature in the range of 55° to 70° C. If the solution is then allowed to cool slowly, a precipitate forms which is easier to separate than when working at low temperatures.

After cooling to below 50° C., the 7-chloro-quinaldine tartrate precipitates as a white precipitate and the tartrate, separated by methods known in themselves, e.g., sedimentation, filtering or centrifuging, and washed with a solvent, is thereafter transformed into the base in a manner known in itself. After cooling to 20° to 25° C., the precipitated 7-chloro-quinaldine can be filtered off and the product obtained is washed with water until neutral and has a 7-chloro-quinaldine content of up to 99%.

This isomer separation can be carried out with the aid of the racemate as well as of the pure enantiomer of tartaric acid, but for economical reasons L(+)-tartaric acid is preferred. Other chemically related acids are unsuitable for the separation, because the respective 7-chloro-quinaldine salts do not precipitate out due to their high solubility or the acids themselves are only slightly soluble, so that salt formation cannot take place.

In the following examples there are described several preferred embodiments to illustrate the invention. However, it should be understood that the invention is not intended to be limited to the specific embodiments.

EXAMPLE 1

Production of 7-chloro-quinaldine 183.7 g of chloroaniline and 88.2 g of 3-chloro-nitrobenzene were added with stirring to 489 ml of 64% sulfuric acid and after heating the mixture to 110° C., 168.2 g of crotonaldehyde were added dropwise over three hours at reflux. The reaction was slightly exothermic and the temperature of the reaction mixture at reflux decreased continuously to 105° C. The mixture was stirred for another 4 hours at reflux temperature. After one hour, the reaction mixture temperature at reflux rose again from 105° to 110° C. and was maintained at 110° C. Thereafter, the mixture was cooled to 30° to 40° C. and 250 ml of water added. The pH was adjusted to 9 with 781 ml of 25% of ammonia water.

After cooling to about 40° C., 250 ml of chloroform were stirred in and the chloroform layer was separated. The aqueous layer was again stirred with 200 ml of chloroform. From the combined chloroform solutions, the solvent was distilled first under normal pressure and at the end, the residual solvent was removed under reduced pressure. Thereafter, the product distilled over at 140° to 185° C. at about 20 hPa and a bath temperature of 160° to 240° C. After the solvent had been distilled off, 350 g of crude product were obtained, and after the distillation, 267 g of distillate and 78 g of residue were obtained. The distillate was semi-solid and of a yellowish to reddish color. The 267 g of distillate contained 74.2 g of 5-chloro-quinaldine and 161.8 g of 7-chloro-quinaldine which corresponded to a total yield of 66.4% and a yield of 7-chloro-quinaldine of 45.5% of the theory.

EXAMPLE 2

Isolation of 7-chloro-quinaldine a) 160 g of L(+)tartaric acid were dissolved in 890 ml of water and 265 g of distillate from Example 1 were dissolved in 1,118 ml of acetone (890 g). The organic solution was filtered and added over 30 minutes with stirring to the tartaric acid solution heated to 60° C. During the addition, the temperature was maintained constant and then the reaction mixture was cooled slowly. At about 50° C., 7-chloro-quinaldine tartarte precipitated as a white precipitate. The mixture was cooled to 18° C., vacuum filtered, and washed with 1,000 ml of acetone at 15° to 18° C., stirred and washed again. After drying at 50° C. in vacuum, 300 g of the white tartrate were obtained.

275 g of the 7-chloro-quinaldine tartrate were suspended in 1,200 ml of water. 94 ml of a 50% caustic soda solution were added dropwise with stirring so slowly that the temperature of 40° C. was not exceeded. After the pH has been adjusted to 9, the mixture was allowed to cool to 20° to 25° C. with the 7-chloro-quinaldine flocculating out. The precipitated product was vacuum filtered, washed neutral with about 1,000 ml of water, and dried in vacuum at 50° C. to obtain 140 g of 99% 7-chloro-quinaldine.

The acetone was removed by distillation from the acetone-containing filtrate whereby an oily dark product separated out, which was taken up in a small amount of chloroform. The chloroform solution contained up to 60% of 5-chloro-quinaldine, 10 to 15% of the 7-chloro-quinaldine and a first run consisting of 3-chloro-quinaldine, 3-chloro-nitro-benene, and many other compounds. The aqueous solution resulting from the splitting of the 7-chloro-quinaldine tartrate contained the disodium salt of tartaric acid and can be used after acidification with hydrochloric acid for the next separation process.

b) The procedure of Step a) was repeated using ethanol as solvent instead of acetone to obtain 120 g of 98% 7-chloro-quinaldine.

c) The procedure of Step a) was repeated using toluene instead of acetone and washing with water and toluene to obtain 115 g of 97% 7-chloro-quinaldine.

d) The procedure of Step a) was repeated using ethyl acette instead of acetone to obtain 140 g of 99% 7-chloro-quinaldine which corresponded to 90% of the 7-chloro-quinaldine used.

Various modifications of the process of the invention may be made without departing from the spirit or scope thereof and it is to be understood that the invention is intended to be limited only as defined in the appended claims.

What we claim is:

1. A process for the recovery of isomeric pure 7-chloroquinaldine from isomeric mixtures of chloro-quinaldines comprising dissolving the isomeric mixture of chloro-quinaldines in an organic solvent, adding an aqueous tartaric acid solution to the organic solution to form the tartrate of 7-chloroquinaldine in crystalline form, recovering the crystals and treating the same with a base to obtain 7-chloro-quinaldine.

2. The process of claim 1 wherein the molar ratio of tartaric acid to the isomeric mixture is 1:1 to 5:1.

3. The process of claim 1 wherein the molar ratio of tartaric acid to the isomeric mixture is 1.1:1 to 2.5:1.

4. The process of claim 1 wherein the organic solvent is water miscible.

5. The process of claim 1 wherein the organic solvent is water-immiscible.

6. The process of claim 1 wherein the organic solvent is selected from the group consisting of ethanol, ethyl acetate and toluene.

7. The process of claim 1 wherein the organic solvent is selected from the group consisting of acetone, methyl ethyl ketone and methyl isobutyl ketone.

8. The process of claim 1 wherein the addition of aqueous tartaric acid solution is effected at room temperature to reflux.

9. The process of claim 8 wherein the temperature is 50° to 80° C.

* * * * *